United States Patent
Obunai et al.

(10) Patent No.: US 12,103,911 B2
(45) Date of Patent: Oct. 1, 2024

(54) METHOD FOR PRODUCING COMPOSITION CONTAINING GALLIC ACID

(71) Applicant: KAO CORPORATION, Tokyo (JP)

(72) Inventors: Ryo Obunai, Wakayama (JP); Yutaka Irie, Wakayama (JP); Sawa Miyake, Wakayama (JP)

(73) Assignee: KAO CORPORATION, Tokyo (JP)

( * ) Notice: Subject to any disclaimer, the term of this patent is extended or adjusted under 35 U.S.C. 154(b) by 530 days.

(21) Appl. No.: 17/620,523

(22) PCT Filed: Jul. 1, 2020

(86) PCT No.: PCT/JP2020/025864
§ 371 (c)(1),
(2) Date: Dec. 17, 2021

(87) PCT Pub. No.: WO2021/002396
PCT Pub. Date: Jan. 7, 2021

(65) Prior Publication Data
US 2022/0356141 A1    Nov. 10, 2022

(30) Foreign Application Priority Data

Jul. 2, 2019   (JP) ................................ 2019-123866

(51) Int. Cl.
*C07C 51/43*  (2006.01)
*C12N 1/20*   (2006.01)
*C12P 7/42*   (2006.01)

(52) U.S. Cl.
CPC ............. *C07C 51/43* (2013.01); *C12N 1/20* (2013.01); *C12P 7/42* (2013.01)

(58) Field of Classification Search
None
See application file for complete search history.

(56) References Cited

U.S. PATENT DOCUMENTS

| | | |
|---|---|---|
| 6,472,190 B1 | 10/2002 | Frost |
| 2010/0173984 A1 | 7/2010 | Zaworotko et al. |
| 2010/0204204 A1* | 8/2010 | Zaworotko .......... A61K 31/522 514/474 |
| 2014/0120593 A1 | 5/2014 | Nukui et al. |
| 2015/0250797 A1 | 9/2015 | Zaworotko et al. |

FOREIGN PATENT DOCUMENTS

| | | |
|---|---|---|
| CN | 103703137 A | 4/2014 |
| JP | 2014-83019 A | 5/2014 |
| WO | WO 2013/111332 A1 | 8/2013 |
| WO | WO 2018/047443 A1 | 3/2018 |
| WO | WO 2018/230011 A1 | 12/2018 |

OTHER PUBLICATIONS

Prasertsit et al., "Possible prebiotics and gallic acid separations from jackfruit seed extract," Songklanakarin J. Sci. Technol., vol. 37, No. 3, 2015, pp. 353-359.
Sun, "Gallic acid production technology (Part 2)," Biomass chemical process, No. 3, Chinese Academy of Forestry, Forestry Chemical Industry Research Institute, 1991, pp. 44-45, with English translation.
International Search Report for PCT/JP2020/025864 (PCT/ISA/210) mailed on Sep. 15, 2020.
Velderrain-Rodríguez et al., "Gallic Acid Content and an Antioxidant Mechanism Are Responsible for the Antiproliferative Activity of 'Ataulfo' Mango Peel on LS180 Cells", Molecules 2018, 23, 695, pp. 1-15.

* cited by examiner

*Primary Examiner* — Sudhakar Katakam
*Assistant Examiner* — Jennifer C Sawyer
(74) *Attorney, Agent, or Firm* — Birch, Stewart, Kolasch & Birch, LLP

(57) ABSTRACT

Provided is a method for producing a composition containing gallic acid, the composition having a low content rate of protocatechuic acid using a microbial culture solution. A method for producing a composition containing gallic acid, the method comprising a step (A) of performing cooling crystallization using an aqueous solution (a) containing gallic acid and protocatechuic acid at 0.9° C./min or less.

12 Claims, No Drawings

METHOD FOR PRODUCING COMPOSITION CONTAINING GALLIC ACID

FIELD OF THE INVENTION

The present invention relates to a method for producing a composition containing gallic acid with low content of protocatechuic acid.

BACKGROUND OF THE INVENTION

Gallic acid (molecular formula: C7H6O5, also known as 3,4,5-trihydroxybenzoic acid) has strong reducing power and is used as a reducing agent, and a photographic developer. Since gallic acid also has a coloring property due to formation of an iron salt, it is also used for producing ink and the like. A number of derivatives such as gallate esters can be obtained from gallic acid, and such derivatives are widely used in various fields such as food field and electronic material field.

Gallic acid has been produced by hydrolyzing tannin extracted from the pentaploid of the plant Nulde using an alkali, an acid, or an enzyme. However, a method for producing gallic acid has been investigated in an industrially advantageous manner because the above method has issues such as a high residual tannin content and high cost for production. Recently, a method for producing gallic acid from an inexpensive raw material such as an aromatic carboxylic acid or glucose using a microorganism has been reported (Patent Literatures 1 and 2).

In Patent Literature 1, an aqueous solution containing gallic acid, produced by culturing a microorganism is cooled once to obtain crude crystals, and then the crude crystals are re-dissolved again to precipitate crystals, thereby obtaining a composition containing gallic acid having a low iron content.

Patent Literature 2 reports that gallic acid was obtained from a fermentation culture solution obtained by using glucose as a raw material by *E. coli* by poor solvent crystallization.

CITATIONS

Patent Literatures (Patent Literature 1) JP-A-2014-83019
(Patent Literature 2) U.S. Pat. No. 6,472,190

SUMMARY OF THE INVENTION

The present invention provides a method for producing a composition containing gallic acid, the method comprising a step (A) of subjecting an aqueous solution (a) containing gallic acid and protocatechuic acid to crystallization under cooling at a rate of 0.9° C./min or less.

DETAILED DESCRIPTION OF THE INVENTION

However, it was found that protocatechuic acid (molecular formula: $C_7H_6O_4$) was contained as a by-product in the microbial culture solution, and protocatechuic acid was also contaminated in the crystals after crystallization.

Accordingly, the present invention relates to a method for producing a composition containing gallic acid with a low content of protocatechuic acid from a microbial culture solution by crystallization.

As a result of energetic studies, the present inventors found that when an aqueous solution containing gallic acid and protocatechuic acid is cooled under a predetermined condition to precipitate crystals, a composition containing gallic acid with low content of protocatechuic acid can be obtained.

The method of the present invention enables to obtain a composition containing gallic acid with low content of protocatechuic acid by using a microorganism.

[Method for Producing Composition Containing Gallic Acid]

The method for producing a composition containing gallic acid of the present invention includes a step (A) of performing cooling crystallization using an aqueous solution (a) containing gallic acid and protocatechuic acid at 0.9° C./min or less.

(Aqueous Solution (a) Containing Gallic Acid and Protocatechuic Acid)

In the present specification, the aqueous solution (a) containing gallic acid and protocatechuic acid is preferably an aqueous solution derived from a culture solution of a microorganism from the viewpoint of industrial productivity.

In the present specification, the microorganism may be any one of a wild-type strain, a mutant strain, or a variant strain in which variation, such as insertion, substitution, or deletion of a base sequence, is caused by various genetic manipulations or may be a strain provided with a gallic acid production ability by a known artificial modification.

Examples of microorganisms having a capability of producing gallic acid include microorganisms such as genera *Escherichia, Rhodococcus, Acinetobacter, Bradyrhizobium, Corynebacterium, Pseudomonas, Rhodopseudomonas, Sinorhizobium, Brevibacterium, Novosphingobium, Ralstonia*.

The medium used for culturing a microorganism capable of producing gallic acid preferably contains a carbon source, an inorganic nitrogen source or an organic nitrogen source, and other necessary organic micronutrient sources that can be assimilated by the microorganism as a culture material. Examples of the culture medium used for culturing include CGXII medium and CGCF medium (WO 2014/007273).

Examples of the carbon source include sugars (glucose, sucrose, maltose, etc.), organic acids, dextran, soluble starch, and methanol.

Examples of the inorganic nitrogen source or the organic nitrogen source include ammonium salts, nitrates, various amino acids, corn steep liquor, tryptone, peptone, casein, yeast extract, meat extract, soybean meal, and potato extract liquid.

The culture medium may include inorganic salts (sodium chloride, calcium chloride, sodium dihydrogenphosphate, potassium dihydrogenphosphate, dipotassium hydrogenphosphate, magnesium chloride, magnesium sulfate, manganese sulfate, etc.), vitamins, antibiotics (tetracycline, neomycin, kanamycin, spectinomycin, erythromycin, etc.).

For culturing the microorganism, a general method can be applied as long as conditions allow the microorganism to grow and produce gallic acid. For example, a medium such as LB medium and CGXII medium can be used for a preliminary preculture and a preculture, and a medium such as CGCF medium can be used for a main culture. The culture temperature is preferably 20° C. or higher and 40° C. or lower, and further more preferably 30° C. or higher and 35° C. or lower.

The pH value of the culture solution during culturing is preferably 4 or more and 8 or less, and further more preferably 5 or more and 7 or less.

The inoculation amount of the microorganism to the medium is preferably 0.1% (v/v) or more and 15% (v/v) or less, and further more preferably 0.5% (v/v) or more and 5% (v/v) or less.

The culturing period of the microorganism can be appropriately set in accordance with the growth of the microorganism, but is preferably 0.5 days or more and 10 days or less, and further more preferably 1 day or more and 5 days or less.

As a culture tank used for culturing, a conventionally known tank can be appropriately adopted. Examples include an aeration stirring-type culture tank, a bubble tower-type culture tank, or a fluidized bed culture tank, which may be performed in any of a batch type, a semi-batch type or a continuous type.

Due to such culture, a microbial culture solution containing gallic acid may be obtained. Protocatechuic acid is contaminated in the culture solution containing gallic acid. Since other impurity components, microbial cells, and unused culture materials are contaminated, separation procedures such as centrifugation, membrane separation, and adsorption separation are performed to obtain the aqueous solution containing gallic acid and protocatechuic acid.

The mass ratio of the content of protocatechuic acid to the content of gallic acid in the aqueous solution (a) containing gallic acid and protocatechuic acid [content of protocatechuic acid/content of gallic acid] is preferably $1\times10^{-4}$ or more, more preferably $1\times10^{-3}$ or more, further more preferably $3\times10^{-3}$ or more from the viewpoint of culturing time of culturing steps and easily receiving the effect of the present invention. From the viewpoint of obtaining gallic acid crystals having a high gallic acid content rate, it is preferably $3\times10^{-1}$ or less, more preferably $1.5\times10^{-1}$ or less, further more preferably $1\times10^{-1}$ or less, and even more preferably $2\times10^{-2}$ or less. The mass ratio of the content of protocatechuic acid to the content of gallic acid in the aqueous solution (a) containing gallic acid and protocatechuic acid [content of protocatechuic acid/content of gallic acid] is preferably $1\times10^{-4}$ or more and $3\times10^{-1}$ or less, more preferably $1\times10^{-3}$ or more and $1.5\times10^{-1}$ or less, further more preferably $3\times10^{-3}$ or more and $1.5\times10^{-1}$ or less, and even more preferably $3\times10^{-3}$ or more and $2\times10^{-2}$ or less.

The content of gallic acid in the aqueous solution (a) containing gallic acid and protocatechuic acid may be less than or equal to a saturated solubility of gallic acid, and is preferably 1 mass % or more, more preferably 2 mass % or more, and further more preferably 2.5 mass % or more from the viewpoint of productivity. From the viewpoint of such as the fluidity of slurry, it is preferably 15 mass % or less, more preferably 12 mass % or less, and further more preferably 11 mass % or less. The content of gallic acid in the aqueous solution (a) containing gallic acid and protocatechuic acid is preferably 1 mass % or more and 15 mass % or less, more preferably 2 mass % or more and 12 mass % or less, and further more preferably 2.5 mass % or more and 11 mass % or less.

The content of protocatechuic acid in the aqueous solution (a) containing gallic acid and protocatechuic acid is preferably 1 mass % or less, more preferably 0.9 mass % or less, and further more preferably 0.8 mass % or less, from the viewpoint of obtaining a composition containing gallic acid having a low rate protocatechuic acid/gallic acid. From the viewpoint of a reaction time in the culturing step, it is preferably 0.0001 mass % or more, more preferably 0.0005 mass % or more, and further more preferably 0.001 mass % or more. The content of protocatechuic acid in the aqueous solution (a) containing gallic acid and protocatechuic acid is preferably 0.0001 mass % or more and 1 mass % or less, more preferably 0.0005 mass % or more and 0.9 mass % or less, and further more preferably 0.001 mass % or more and 0.8 mass % or less.

(Cooling Crystallization)

The precipitation of the composition containing gallic acid can be performed by cooling the aqueous solution (a) containing gallic acid and protocatechuic acid. In the present invention, the aqueous solution (a) is cooled under the condition that an average cooling rate from the cooling start temperature to the cooling finish temperature is 0.9° C./min or less.

(Average Cooling Rate)

In the present specification, the average cooling rate may be defined by, dividing the difference between the temperature of the start of cooling and the temperature of the end of cooling (° C.) by the time required to reach the temperature of the end of cooling from the temperature of the start of cooling (min). The average cooling rate is 0.9° C./min or less, preferably 0.5° C./min or less, more preferably 0.3° C./min or less, further more preferably 0.1° C./min or less, from the viewpoint of suppressing contamination of protocatechuic acid in the crystal, to obtain a composition with low ratio of protocatechuic acid/gallic acid, and is preferably 0.005° C./min or more, more preferably 0.01° C./min or more, and further more preferably 0.02° C./min or more from the viewpoint of cycle time. The average cooling rate is 0.9° C./min or less, preferably 0.005° C./min or more and 0.5° C./min or less, more preferably 0.01° C./min or more and 0.3° C./min or less, further more preferably 0.02° C./min or more and 0.1° C./min or less.

(Step (P1): Raising the Temperature of the Aqueous Solution (a))

Since gallic acid has high solubility at high temperature, in the present invention, it is preferable that the dissolved gallic acid concentration is increased by the step (P1) of raising the temperature of the aqueous solution (a) containing gallic acid and protocatechuic acid before cooling, and then cooling is performed. The temperature of raising temperature, i.e., the temperature of the aqueous solution (a) containing gallic acid and protocatechuic acid before cooling (temperature at which cooling starts), from the viewpoint of increasing the yield of the composition containing gallic acid, it is preferably 60° C. or higher, more preferably 70° C. or higher, further more preferably 80° C. or higher, and from the viewpoint of evaporation of water, preferably 100° C. or lower, more preferably 90° C. or less, and further more preferably 85° C. or lower. The temperature of raising temperature is preferably 60° C. or higher and 100° C. or lower, more preferably 70° C. or higher and 90° C. or lower, further more preferably 80° C. or higher and 85° C. or lower.

(Cooling Temperature)

The temperature of ending cooling is preferably 50° C. or lower, more preferably 40° C. or lower, further more preferably 30° C. or lower, from the viewpoint of enhancing the yield of the composition containing gallic acid, and is preferably 0° C. or higher, more preferably 5° C. or higher, and further more preferably 10° C. or higher from the viewpoint of coagulation of water. The temperature of ending cooling is preferably 0° C. or higher and 50° C. or less, more preferably 5° C. or higher and 40° C. or less, further more preferably 10° C. or higher and 30° C. or less.

(Crystallization Apparatus)

The precipitation of the composition containing gallic acid is preferably performed by stirring using a reaction tank having a stirring blade. The stirring blade may assume any shape, but it is preferably a paddle blade, a turbine blade, a propeller blade, an anchor blade, a large blade diameter paddle blade, and a max blend blade, especially for better mixing of the crystals. The peripheral speed of the stirring is preferably 0.2 m/s or more, more preferably 0.3 m/s or more, and further more preferably 0.5 m/s or more from the viewpoint of preventing the slurry from caking, and is preferably 10 m/s or less, more preferably 5 m/s or less, and further more preferably 3 m/s or less from the viewpoint of uniformly crystallizing the composition containing gallic acid having a large particle diameter.

(Step (P2): Adjusting the pH Value of the Aqueous Solution (a) to 4.5 or Less)

In the present invention, from the viewpoint of enhancing the yield of the composition containing gallic acid, it is preferable to perform the step (P2) of adjusting the pH value of the aqueous solution (a) containing gallic acid and protocatechuic acid to 4.5 or less before cooling. The pH value of the aqueous solution (a) containing gallic acid and protocatechuic acid at the time of precipitating the composition containing gallic acid is not particularly limited, but is preferably 4.5 or less, more preferably 4.0 or less, further more preferably 3.5 or less, from the viewpoint of enhancing the yield of the composition containing gallic acid, and is preferably 1.5 or more, more preferably 2.0 or more, and further more preferably 2.5 or more from the viewpoint of apparatus corrosion. The pH value of the aqueous solution (a) containing gallic acid and protocatechuic acid is preferably 1.5 or more and 4.5 or less, more preferably 2.0 or more and 4.0 or less, and further more preferably 2.5 or more and 3.5 or less. For adjusting the pH value of the aqueous solution, for example, an inorganic acid such as hydrochloric acid, nitric acid, sulfuric acid, or phosphoric acid can be used. In the present invention, it is preferable to implement the step (P1) of raising the temperature of the aqueous solution (a) containing gallic acid and protocatechuic acid, the step (P2) of adjusting the pH value of the aqueous solution (a) to 4.5 or less, and the step (A) of performing cooling crystallization of the aqueous solution (a) at 0.9° C./min or less in this order, from the viewpoint of enhancing the yield of the composition containing gallic acid.

(Preparation, Washing of Composition Containing Gallic Acid)

The composition containing gallic acid precipitated by cooling can be separated by a solid-liquid separation such as batch centrifugal filtration, continuous centrifugal filtration, or filter press. During the solid-liquid separation, the composition containing gallic acid may be washed if necessary. Examples of the solvent used for washing include water, ethanol, acetone, and toluene. The ratio of the volume of the solvent to the volume of the fractioned composition containing gallic acid is preferably 1.0 or more, more preferably 2.0 or more, and further more preferably 3.0 or more, from the viewpoint of obtaining a composition containing gallic acid having less impurities, and is preferably 5.0 or less, more preferably 4.5 or less, and further more preferably 3.5 or less from the viewpoint of enhancing the yield of the composition containing gallic acid.

(Drying of Composition Containing Gallic Acid)

The method for drying the composition containing gallic acid is not particularly limited as long as it can remove water, and a conventional dryer such as a shelf dryer, a conical dryer, a paddle dryer, a nauter mixer, a fluidized bed dryer, a vacuum stirring dryer, a disc dryer can be used. From the viewpoint of suppressing coloring of the composition containing gallic acid, vacuum stirring drying is preferable. The drying temperature is preferably −30° C. or higher, more preferably −20° C. or higher, further more preferably −10° C. or higher, and is preferably 90° C. or lower, more preferably 80° C. or lower, and further more preferably 70° C. or lower. If necessary, the composition containing gallic acid may be subjected to a treatment such as sieving after drying.

[Composition Containing Gallic Acid]

The composition containing gallic acid obtained by the method of the present invention has a lower content ratio of protocatechuic acid than a protocatechuic acid content ratio in an aqueous solution (a) containing gallic acid and protocatechuic acid. The mass ratio of the content of protocatechuic acid to the content of gallic acid in the composition containing gallic acid [the content of protocatechuic acid/the content of gallic acid] is preferably 0.05 or less, more preferably 0.03 or less, and further more preferably 0.01 or less, from the viewpoint of availability of the composition containing gallic acid. The composition containing gallic acid having a low protocatechuic acid content is improved in solubility because the crystals become needle-like compared with gallic acid containing no protocatechuic acid. The mass ratio of the content of protocatechuic acid to the content of gallic acid in the composition containing gallic acid [the content of protocatechuic acid/the content of gallic acid] is preferably 0.001 or more, more preferably 0.003 or more, from the viewpoint of solubility of the composition containing gallic acid. The mass ratio of the content of protocatechuic acid to the content of gallic acid in the composition containing gallic acid [the content of protocatechuic acid/the content of gallic acid] is preferably 0.001 or more and 0.05 or less, more preferably 0.003 or more and 0.03 or less, and further more preferably 0.003 or more and 0.01 or less.

From the viewpoint of solubility of the composition containing gallic acid, the average crystal particle diameter of the composition containing gallic acid is preferably 8 μm or less, more preferably 6 μm or less, and further more preferably 4 μm or less. In the present specification, a phase-contrast microscopy (Nikon ECLIPSE80i, manufactured by Nikon Corporation) is used for crystal observation, and an image integration software NIS-ElementsD is used for measuring crystal minor axis.

A composition containing gallic acid having a low content of protocatechuic acid is useful as a raw material for producing various derivatives in addition to its own use.

EXAMPLES

[Measurement Method of Content of Gallic Acid and Protocatechuic Acid]

The sample to be measured was dried, 15 mg of the dried sample was dissolved in 50 mL of a 0.085 N sulfuric acid aqueous solution, and the concentration of each component was quantified by liquid chromatography. The gallic acid and protocatechuic acid in the culture solution were diluted 200 times with the 0.085 N sulfuric acid aqueous solution and then quantified by liquid chromatography.

(Analysis Conditions)

Analysis conditions for liquid chromatography are column: L-column ODS, eluent A: 0.1 M $KH_2PO_4$·0.1% (v/v) $H_3PO_4$ aqueous solution, eluent B: 70% (v/v) methanol aqueous solution, eluent switching: eluent A/eluent B=from 100/0 to 0/100 in 5-20 min separated by gradient, detector: DAD, column temperature: 40° C., and injection volume: 5 μL.

[pH Measurement Method]

The pH value of an aqueous solution (undiluted) at 70° C. was measured by using F-50 manufactured by HORIBA, Ltd.

Comparative Example 1

(Construction of Gallic Acid-Producing Bacteria)

A plasmid that functions in *Corynebacterium glutamicum*, in which the HFM145_L200V_Y385F (JP-B-5142268) is expressed, was introduced into the NSHAaroE3_vanE3ΔqsuB Pben-qsuB-vanR Ptu-tkt strain (JP-B-6322576) which is a protocatechuic acid-producing bacteria being a precursor of gallic acid, by using transformation by electroporation to obtain a *Corynebacterium glutamicum* TY1030 strain that produces gallic acid.

(Culturing Method)

The *Corynebacterium glutamicum* TY1030 strain was used as a bacterial cell.

A 10 L medium (described below) was charged in a 30 L aeration stirring tank, and the bacterial cell was inoculated such that the OD600 reached 2.5. The culture was performed by using a 30 L aeration stirring tank (MITSUWA FRONTECH CORP.), a stirring speed was controlled in the range from 100 to 650 r/min, and the aeration amount was controlled in the range from 3 to 30 L-Air/min. For a sugar feed, 8 kg of a 60% (w/w) glucose aqueous solution was prepared, and the sugar feed was performed at 200 g-solution weight/h from 5 hours after the start of the culture. The pH value was controlled to 6.5 with 14% aqueous ammonia. The culturing was performed under conditions at 32° C. and 0.04 MPa for 2 days.

(Medium)
- 2.5% (w/v) glucose
- 1% (w/v) ammonium sulfate
- 0.5% (w/v) corn steep liquor
- 0.1% (w/v) dipotassium hydrogenphosphate
- 0.1% (w/v) potassium dihydrogenphosphate
- 0.012% (w/v) anhydrous citric acid
- 0.0144% (w/v) sodium benzoate
- 0.025% (w/v) magnesium sulfate
- 0.25% (w/v) SHOHOZAI NO. 1 (DEFOAMER NO. 1, Kao Corporation)
- 0.005% (w/v) kanamycin sulfate After culturing, the pH value of the culture solution was adjusted to 4.0 with concentrated sulfuric acid, and the bacterial cell and the culture solution were separated by centrifugation. The obtained culture solution was passed through a 0.2 μm membrane filter to separate impurity components, and the aqueous solution was obtained. The gallic acid (GAL) concentration in the obtained aqueous solution was 81.3 g/L, and the concentration of protocatechuic acid (PCA) was 6.8 g/L. The mass ratio of the content of protocatechuic acid to the content of gallic acid in the aqueous solution [protocatechuic acid/gallic acid] was 0.084.

The precipitation of the composition containing gallic acid was performed in a jacket-type reaction tank with a paddle blade having a blade diameter of 14 cm and an internal volume of 3000 mL at the stirring speed of 140 r/min.

First, 2,250 g of the aqueous solution obtained by the above method was heated to 70° C. Subsequently, the pH value was adjusted to 2.6 with the 60% sulfuric acid aqueous solution. Next, crystals were precipitated by cooling the aqueous solution to 15° C. so that the average cooling rate from 70° C. to 15° C. was 3.0° C./min.

The obtained suspension was suction-filtered, and the obtained cake in an amount of 125 mL was washed with 500 mL of distilled water, and then freeze-dried overnight to obtain a composition containing gallic acid.

The mass ratio of the content of protocatechuic acid to the content of gallic acid in the composition containing gallic acid [protocatechuic acid/gallic acid] was 0.067.

Example 1

In Comparative Example 1, the same procedure as in Comparative Example 1 was performed except that cooling was performed so that the average cooling rate from 70° C. to 15° C. was 0.3° C./min.

The mass ratio of the content of protocatechuic acid to the content of gallic acid in the composition containing gallic acid [protocatechuic acid/gallic acid] was 0.026.

Example 2

In Comparative Example 1, the same procedure as in Comparative Example 1 was performed except that cooling was performed so that the average cooling rate from 70° C. to 15° C. was 0.04° C./min.

The mass ratio of the content of protocatechuic acid to the content of gallic acid in the composition containing gallic acid [protocatechuic acid/gallic acid] was 0.016.

Example 3

In Comparative Example 1, the same procedure as in Comparative Example 1 was performed except that cooling was performed so that the average cooling rate from 70° C. to 15° C. was 0.02° C./min.

The mass ratio of the content of protocatechuic acid to the content of gallic acid in the composition containing gallic acid thus obtained [protocatechuic acid/gallic acid] was 0.020.

Example 4

In Comparative Example 1, the same procedure as in Comparative Example 1 was performed except that cooling was performed so that the average cooling rate from 70° C. to 15° C. was 0.9° C./min.

The mass ratio of the content of protocatechuic acid to the content of gallic acid in the composition containing gallic acid thus obtained [protocatechuic acid/gallic acid] was 0.038.

The results are shown in Table 1.

TABLE 1

| | Aqueous solution condition | | | Crystallization condition | | | GAL containing composition |
|---|---|---|---|---|---|---|---|
| | GAL concentration [g/L] | PCA concentration [g/L] | PCA/GAL [g/g] | Scale [L] | Cooling rate [° C./min] | Stirring speed [r/min] | PCA/GAL [g/g] |
| Comparative Example 1 | 81.3 | 6.8 | 0.084 | 3.00 | 3.00 | 140.0 | 0.067 |
| Example 1 | 82.9 | 6.9 | 0.083 | 3.00 | 0.30 | 140.0 | 0.026 |
| Example 2 | 81.3 | 6.8 | 0.084 | 3.00 | 0.04 | 140.0 | 0.016 |
| Example 3 | 78.1 | 6.4 | 0.082 | 3.00 | 0.02 | 140.0 | 0.020 |
| Example 4 | 81.3 | 6.8 | 0.084 | 3.00 | 0.90 | 140.0 | 0.038 |

Comparative Example 2

Water and a gallic acid reagent (gallic acid monohydrate, manufactured by FUJIFILM Wako Pure Chemical Corporation) were added to Mighty Vial No. 8, and gallic acid was completely dissolved at 70° C. The concentration of gallic acid in the obtained aqueous solution was 75.5 g/L. The mass ratio of the content of protocatechuic acid to the content of gallic acid in the aqueous solution [protocatechuic acid/gallic acid] was 0.000.

The precipitation of the composition containing gallic acid was performed in a temperature controllable thermostatic tank under static conditions.

Crystals were precipitated by cooling the aqueous solution to 20° C. so that the average cooling rate from 70° C. to 20° C. was 0.3° C./min.

The obtained suspension was passed through a 0.2 μm membrane filter to separate crystalline components, and the contents of gallic acid and protocatechuic acid in the obtained filtrate were measured. The mass ratio of the content of protocatechuic acid to the content of gallic acid in a gallic acid-containing crystal composition calculated from the contents of gallic acid and protocatechuic acid in the aqueous solution [protocatechuic acid/gallic acid] was 0.000. The average crystal minor diameter was 14.0 μm.

Example 5

In Comparative Example 2, the same procedure as in Comparative Example 2 was performed except that a protocatechuic acid reagent (protocatechuic acid, manufactured by FUJIFILM Wako Pure Chemical Corporation) was added to the gallic acid reagent.

The concentration of gallic acid in the obtained aqueous solution was 74.3 g/L, that of protocatechuic acid was 0.5 g/L, and the mass ratio of the content of protocatechuic acid to the content of gallic acid [protocatechuic acid/gallic acid] was 0.007.

The mass ratio of the content of protocatechuic acid to the content of gallic acid in the composition containing gallic acid [protocatechuic acid/gallic acid] was 0.004. The average crystal minor diameter was 3.3 μm.

Example 6

In Example 5, the same procedure as in Example 5 was performed except that the amount of protocatechuic acid reagent to be added was changed.

The concentration of gallic acid in the obtained aqueous solution was 71.2 g/L, that of protocatechuic acid was 1.0 g/L, and the mass ratio of the content of protocatechuic acid to the content of gallic acid [protocatechuic acid/gallic acid] was 0.014.

The mass ratio of the content of protocatechuic acid to the content of gallic acid in the composition containing gallic acid (protocatechuic acid/gallic acid) was 0.007. The average crystal minor diameter was 5.2 μm.

Example 7

In Example 5, the same operation as in Example 5 was performed except that the amount of protocatechuic acid reagent to be added was changed.

The concentration of gallic acid in the obtained aqueous solution was 75.3 g/L, that of protocatechuic acid was 3.2 g/L, and the mass ratio of the content of protocatechuic acid to the content of gallic acid [protocatechuic acid/gallic acid] was 0.042.

The mass ratio of the content of protocatechuic acid to the content of gallic acid in the composition containing gallic acid [protocatechuic acid/gallic acid] was 0.023. The average crystal minor diameter was 10.9 μm.

Example 8

In Example 5, the same operation as in Example 5 was performed except that the amount of protocatechuic acid reagent to be added was changed.

The concentration of gallic acid in the obtained aqueous solution was 75.6 g/L, that of protocatechuic acid was 5.4 g/L, and the mass ratio of the content of protocatechuic acid to the content of gallic acid [protocatechuic acid/gallic acid] was 0.071.

The mass ratio of the content of protocatechuic acid to the content of gallic acid in the composition containing gallic acid [protocatechuic acid/gallic acid] was 0.038. The average crystal minor diameter was 10.2 μm.

TABLE 2

| | Aqueous solution condition | | | Crystallization condition | | GAL containing composition | |
|---|---|---|---|---|---|---|---|
| | GAL concentration [g/L] | PCA concentration [g/L] | PCA/GAL [g/g] | Scale [mL] | Cooling rate [° C./min] | PCA/GAL [g/g] | Average crystal minor diameter μm |
| Comparative Example 2 | 75.5 | 0.0 | 0.000 | 50 | 0.30 | 0.000 | 14.0 |
| Example 5 | 74.3 | 0.5 | 0.007 | 50 | 0.30 | 0.004 | 3.3 |
| Example 6 | 71.2 | 1.0 | 0.014 | 50 | 0.30 | 0.007 | 5.2 |
| Example 7 | 75.3 | 3.2 | 0.042 | 50 | 0.30 | 0.023 | 10.9 |
| Example 8 | 75.6 | 5.4 | 0.071 | 50 | 0.30 | 0.038 | 10.2 |

As is evident from Tables 1 and 2, it was confirmed that a composition containing gallic acid with low content of protocatechuic acid can be obtained by cooling an aqueous solution containing gallic acid and protocatechuic acid at an average cooling rate of at 0.9° C./min or less. It was also confirmed that the composition containing gallic acid with low content of protocatechuic acid gives a needle-like crystal compared with gallic acid containing no protocatechuic acid.

The invention claimed is:
1. A method for producing a composition containing gallic acid, the method comprising a step (A) of performing cooling crystallization using an aqueous solution (a) containing gallic acid and protocatechuic acid at 0.9° C./min or less.

2. The method for producing the composition containing gallic acid according to claim 1, wherein a mass ratio of a protocatechuic acid content to a gallic acid content of the gallic acid-containing composition is 0.05 or less.

3. The method for producing the composition containing gallic acid according to claim 1, wherein a mass ratio of a protocatechuic acid content to a gallic acid content of the composition containing gallic acid is 0.001 or more and 0.01 or less.

4. The method for producing the composition containing gallic acid according to claim 1, wherein a mass ratio of a protocatechuic acid content to a gallic acid content of the aqueous solution (a) is $1\times10^{-4}$ or more and $3\times10^{-1}$ or less.

5. The method for producing the composition containing gallic acid according to claim 1, wherein a mass ratio of a protocatechuic acid content to a gallic acid content of the aqueous solution (a) is $1\times10^{-4}$ or more and $1.5\times10^{-1}$ or less.

6. The method for producing the composition containing gallic acid according to claim 1, wherein a mass ratio of a protocatechuic acid content to a gallic acid content of the aqueous solution (a) is $3\times10^{-3}$ or more and $2\times10^{-2}$ or less.

7. The method for producing the composition containing gallic acid according to claim 1, wherein the aqueous solution (a) derives from a culture solution of a microorganism.

8. The method for producing the composition containing gallic acid according to claim 7, wherein the microorganism is a microorganism belonging to the genus *Corynebacterium*.

9. The method for producing the composition containing gallic acid according to claim 1, comprising a step (P1) before the step (A):
   step (P1): raising the temperature of the aqueous solution (a).

10. The method for producing the composition containing gallic acid according to claim 1, wherein a temperature at which cooling is started is 60° C. or higher and 100° C. or lower, and a temperature at which cooling is finished is 0° C. or higher and 50° C. or lower.

11. The method for producing the composition containing gallic acid according to claim 1, comprising a step (P2) before the step (A):
   step (P2): adjusting the pH value of the aqueous solution (a) to 4.5 or less.

12. The method for producing the composition containing gallic acid according to claim 1, comprising a step (P1) and a step (P2) before the step (A):
   step (P1): raising the temperature of the aqueous solution (a), and
   step (P2): adjusting the pH value of the aqueous solution (a) to 4.5 or less; and
   wherein the step (P1), the step (P2), and the step (A) are performed in this order.

* * * * *